US011278591B2

(12) United States Patent
Bortz

(10) Patent No.: US 11,278,591 B2
(45) Date of Patent: Mar. 22, 2022

(54) COMPOSITIONS COMPRISING CHOLINE

(71) Applicant: Balchem Corporation, New Hampton, NY (US)

(72) Inventor: Jonathan Bortz, New Hampton, NY (US)

(73) Assignee: Balchem Corporation, New Hampton, NY (US)

( * ) Notice: Subject to any disclaimer, the term of this patent is extended or adjusted under 35 U.S.C. 154(b) by 128 days.

(21) Appl. No.: 16/087,521

(22) PCT Filed: Mar. 20, 2017

(86) PCT No.: PCT/US2017/023195
§ 371 (c)(1),
(2) Date: Sep. 21, 2018

(87) PCT Pub. No.: WO2017/165287
PCT Pub. Date: Sep. 28, 2017

(65) Prior Publication Data
US 2019/0125828 A1    May 2, 2019

Related U.S. Application Data

(60) Provisional application No. 62/311,590, filed on Mar. 22, 2016.

(51) Int. Cl.
| | | |
|---|---|---|
| *A61K 38/17* | (2006.01) | |
| *A61K 31/14* | (2006.01) | |
| *A61K 31/714* | (2006.01) | |
| *A61K 33/26* | (2006.01) | |
| *A61K 9/20* | (2006.01) | |
| *A61K 31/194* | (2006.01) | |
| *A61K 45/06* | (2006.01) | |
| *A61K 31/122* | (2006.01) | |
| *A61K 33/06* | (2006.01) | |
| *A61K 31/519* | (2006.01) | |
| *A61K 47/54* | (2017.01) | |

(52) U.S. Cl.
CPC ........ *A61K 38/1709* (2013.01); *A61K 9/2054* (2013.01); *A61K 31/122* (2013.01); *A61K 31/14* (2013.01); *A61K 31/194* (2013.01); *A61K 31/519* (2013.01); *A61K 31/714* (2013.01); *A61K 33/06* (2013.01); *A61K 33/26* (2013.01); *A61K 45/06* (2013.01); *A61K 47/547* (2017.08)

(58) Field of Classification Search
None
See application file for complete search history.

(56) References Cited

U.S. PATENT DOCUMENTS

| | | | |
|---|---|---|---|
| 5,567,736 A | 10/1996 | Buchman et al. | |
| 5,574,018 A * | 11/1996 | Habberfield | A61K 47/551 |
| | | | 424/85.4 |
| 7,429,569 B2 * | 9/2008 | Halevie-Goldman | |
| | | | A61P 35/00 |
| | | | 514/43 |
| 2004/0086564 A1 * | 5/2004 | Richardson | A61K 9/2081 |
| | | | 424/469 |
| 2005/0171034 A1 | 8/2005 | Halevie-Goldman | |
| 2008/0139570 A1 | 6/2008 | Chisholm et al. | |
| 2009/0035385 A1 | 2/2009 | Bortz | |
| 2011/0251149 A1 | 10/2011 | Perrine et al. | |
| 2012/0322719 A1 | 12/2012 | Pavlov et al. | |
| 2014/0271982 A1 * | 9/2014 | Fernandez | A61K 31/375 |
| | | | 426/2 |
| 2015/0132273 A1 | 5/2015 | Daniels | |

FOREIGN PATENT DOCUMENTS

| | | |
|---|---|---|
| EP | 0595005 A1 | 5/1994 |
| WO | 2018106921 A1 | 6/2018 |

OTHER PUBLICATIONS

Zeisel, Steven H. "Nutrition in pregnancy: the argument for including a source of choline." International journal of women's health 5 (2013): 193-199.*
Fedosov, Sergey N., et al. "Human intrinsic factor expressed in the plant *Arabidopsis thaliana*." European Journal of Biochemistry 270.16 (2003): 3362-3367.*
Hvas, Anne-Mette, et al. "The effect of recombinant human intrinsic factor on the uptake of vitamin B12 in patients with evident vitamin B12 deficiency." haematologica 91.6 (2006): 805-808.*
Examination Report dated Oct. 19, 2020 in EP 17770902.9, 5 pages.
Examination Report dated Aug. 30, 2020 in EP 17770902.9, 7 pages.
International Preliminary Report on Patentability dated Jun. 16, 2017 for PCT/US2017/23195, 10 pages.
Song et al., "Effects of choline on sodium arsenite-induced neural tube defects in chick embryos," Food and Chemical Toxicology, 2012, 50: 4364-4373.
Zeisel et al., "Nutrition in pregnancy: the argument for including a source of choline," International Journal of Women's Health, 2013, 5: 193-199.
Examination Report dated Oct. 23, 2019 in EP 17770902.9, 9 pages.
Yan et al., "Pregnancy alters choline dynamics: results of a randomized trial using stable isotope methodology in pregnant and nonpregnant women," Am J Clin Nutr, 2013, pp. 1459-1467, vol. 98, No. 6.
Examination Report dated Apr. 15, 2021 in BR 112018069285-9, 5 pages.
Fedosov, et al. "Human intrinsic factor expressed in the plant *Arabidopsis thaliana*," Eur. J. Biochem. 270(16):3362-3367 (2003).
Hvas, et al. "The effect of recombinant human intrinsic factor on the uptake of vitamin B12 in patients with evident vitamin B12 deficiency," Haematologica 91(6):805-808 (2006).

(Continued)

*Primary Examiner* — Bethany P Barham
*Assistant Examiner* — Peter Anthopolos
(74) *Attorney, Agent, or Firm* — Polsinelli PC

(57) ABSTRACT

The present disclosure provides a single dose form composition to optimize the relationship between the 'Folate-Cobalamin' and 'Choline-Betaine' pathways. Single dose form compositions disclosed herein ensure an adequate intake of the rate limiting compounds that have been demonstrated to reduce the efficiency of this vital metabolic axis, and methods of use thereof.

20 Claims, No Drawings

(56) References Cited

OTHER PUBLICATIONS

Examination Report dated Apr. 7, 2021 in CN 2017800300910.6, 12 pages.
Zhang, et al., "Practical Ophthalmic Pharmacology," People's Military Medical Press, p. 413.
Examination Report dated Oct. 10, 2020 in CN 201780030910.6, 25 pages.
Examination Report dated Dec. 18, 2020 in MX/a/2018/011270, 7 pages.
Allen et al., "Isolation of Gastric Vitamin B12-binding Proteins Using Affinity Chromatography," J Biol Sci, 1973, pp. 3660-3669, vol. 248, No. 10.
Office Action for Korean Patent Application 10-2018-7028660 dated Jun. 29, 2021, 7 pages.
Office Action for Mexican Patent Application MX/a/2018/011270 dated Jun. 9, 2021, 6 pages.

* cited by examiner

COMPOSITIONS COMPRISING CHOLINE

CROSS REFERENCE TO RELATED APPLICATIONS

This application claims priority to PCT Application No. PCT/US2017/023195, filed Mar. 20, 2017, which claims the benefit of U.S. provisional application No. 62/311,590, filed Mar. 22, 2016, the disclosures of which are hereby incorporated by reference in their entirety.

FIELD OF THE INVENTION

The present disclosure provides a single dosage form composition to optimize the relationship between the 'Folate-Cobalamin' and 'Choline-Betaine' pathways. Single dosage form compositions disclosed herein ensure an adequate intake of the rate limiting compounds that have been demonstrated to reduce the efficiency of this vital metabolic axis, and methods of use thereof.

BACKGROUND OF THE INVENTION

Choline is an essential nutrient and the liver is a central organ responsible for choline metabolism. Choline is a constituent of cell and mitochondrial membranes and of the neurotransmitter acetylcholine. Choline also influences diverse processes such as lipid metabolism, signaling through lipid second messengers, methylation-dependent biosynthesis of molecules (including epigenetic regulation of gene expression), activation of nuclear receptors, enterohepatic circulation of bile and cholesterol, plasma membrane fluidity, and mitochondrial bioenergetics. See, for example, Corbin et al, *Curr Opin Gastorenterol.* 2012, 28(2):159-165.

The two major fates for choline are (1) phosphorylation and use in phospholipids, and (2) oxidation and use as a donor of methyl-groups. As discussed further below, choline deficiency is associated with liver dysfunction and other diseases and conditions. Choline deficiency, however, can result not just from inadequate intake of choline. Importantly, the fate of choline is highly dependent upon the availability of vitamin B12.

An especially important choline metabolite in liver is phosphatidylcholine, which is necessary for the packaging and export of triglycerides in very low density lipoprotein (VLDL) and for the solubilization of bile salts for secretion. Aberrant VLDL-mediated secretion of triglycerides is a central mechanism in hepatic steatosis. The role of bile homeostasis in liver physiology is also quite evident, and mostly relates to the causes of gallstones, fibrosis, and hepatocarcinomas. However, new functions attributed to bile salts, including regulation of energy and glucose metabolism, makes it likely that phosphatidylcholine plays a role in modulating these functions as well.

Choline, folate and methionine metabolism are interrelated as all influence the production of S-adenosylmethionine, the universal donor of methyl-groups in biological reactions. Deficiency in one nutrient is associated with an increase in flux of the other nutrients towards methyl donation. Methyl donation, in other words, is the pathway that seems to take priority over other functions of both choline and its derivatives (e.g. betaine) and folate, and when one is deficient, the other pathway dominates in the production of methyl groups for single carbon metabolism.

Several mouse models with deletion of choline-related genes have given insight into the mechanisms of NAFLD. In several mouse models, deletion of genes needed to use choline as a methyl donor (Bhmt, Chdh), deletion of genes needed to form the choline moiety endogenously (PEMT) or deletion of genes needed to make S-adenosylmethionine (Mat1) result in fatty liver. In humans, polymorphisms in PEMT are associated with NAFLD. These observations suggest that the methyl-donation function of choline is important in the mechanism of NAFLD. Also phosphatidylcholine that is derived from the PEMT methylation pathway is required for normal VLDL secretion from liver.

Choline is also an important part of the mitochondrial membrane and mitochondrial dysfunction is a central mechanism in the pathogenesis of NAFLD. Low choline may be important in NAFLD pathophysiology because it perturbs mitochondrial bioenergetics and fatty acid beta oxidation. Endoplasmic reticulum (ER) stress is a condition whereby excess unfolded proteins lead to a cascade of stress responses. If stress is chronic, cell death can occur. ER stress is believed to play a role in the pathogenesis of NAFLD. In mice fed methionine-choline deficient diets for up to 21 days, hepatic steatosis was associated with inducing specific ER stress cascades upstream of the unfolded protein response. The integrated ER stress response was unable to cause liver injury in the absence of steatosis, suggesting a coordinated mechanism is necessary for liver disease progression.

Stress within the cell is also contributed to by the presence of excess iron, which, by its very nature of inducing oxidative and other metabolic phenomena of stress. Iron accumulation is a frequent finding in subjects with hepatocellular carcinogenesis, colonic neoplasia, colorectal carcinogenesis, fatty liver disease, nonalcoholic steatohepatitis, insulin resistance, type I and type II diabetes, atherosclerosis, and dysmetabolic iron overload syndrome. This may be in part another consequence of choline deficiency as choline has been shown to reduce the number of ferroportin transporters in the membrane wall of the liver cell and with ferroportin being the only identified iron exporter from the liver cell, this may contribute to the entrapment of iron within the hepatocytes.

Folate is an essential B vitamin required for many one-carbon reactions involved in phospholipid, DNA, protein, and neurotransmitter syntheses. Either 5-methyltetrahydrofolate or betaine, an oxidized form of choline, can supply methyl groups to methylate homocysteine to methionine. Methionine is then converted to S-adenosylmethionine (SAM), the methyl donor for many biological methylation reactions. This cycle is necessary to maintain availability of the methyl donor S-adenosylmethionine; interruption reduces the wide range of methylated products. One such important methylation is that of myelin basic protein. Reductions in the level of S-adenosylmethionine due to vitamin $B_{12}$ deficiency produce demyelination of the peripheral nerves and the spinal column, called sub-acute combined degeneration. The other principal presenting condition is a megaloblastic anemia morphologically identical to that seen in folate deficiency. Disruption of the methylation cycle should cause a lack of DNA biosynthesis and anemia.

The key enzyme that methylates homocysteine to form methionine is methionine synthase, which can only accept a methyl group from cobalamin (vitamin B12) and not from folate, and hence, cobalamin is an essential co-factor in this critical methylation step. The criticality of this co-factor is highlighted by what has become known as the Methyl Folate Trap. Whereas choline is a methyl-rich compound, and is therefore a methyl donor, folate and cobalamin are only methyl intermediaries that accept a methyl group from the intracellular environment (i.e. betaine derived methyl groups) and transfer it in the case of folate to cobalamin and in the case of cobalamin to homocysteine to synthesize methionine.

The methyl folate trap hypothesis is based on the fact that once the cofactor 5,10-methylenetetrahydrofolate is reduced by its reductase to form 5-methyltetrahydrofolate, the reverse reaction cannot occur. This suggests that the only way for the methyltetrahydrofolate to be recycled to tetrahydrofolate, and thus to participate in DNA biosynthesis and cell division, is through the vitamin $B_{12}$-dependent enzyme methionine synthase. When the activity of this synthase is compromised the cellular folate will become progressively trapped as 5-methyltetrahydrofolate. This will result in a cellular pseudo folate deficiency where despite adequate amounts of folate an anemia will develop that is identical to that seen in true folate deficiency. Clinical symptoms of cobalamin deficiency, therefore, include neuropathy, anemia, or both. Treatment with vitamin $B_{12}$, if given intramuscularly, will reactivate methionine synthase, allowing myelination to restart. The trapped folate will be released and DNA synthesis and generation of red cells will cure the anemia. Treatment with high concentrations of folic acid will treat the anemia but not the neuropathy.

Most microorganisms, including bacteria and algae, synthesize vitamin $B_{12}$, and they constitute the only source of the vitamin. The vitamin $B_{12}$ synthesized in microorganisms enters the human food chain through incorporation into food of animal origin. In many animals gastrointestinal fermentation supports the growth of these vitamin $B_{12}$-synthesising microorganisms, and subsequently the vitamin is absorbed and incorporated into the animal tissues. This is particularly true for the liver, where vitamin $B_{12}$ is stored in large concentrations. Products from these herbivorous animals, such as milk, meat, and eggs, constitute important dietary sources of the vitamin unless the animal is subsisting in one of the many regions known to be geochemically deficient in cobalt. Milk from cows and humans contains binders with very high affinity for vitamin $B_{12}$, whether they hinder or promote intestinal absorption is not entirely clear. Omnivores and carnivores, including humans, derive dietary vitamin $B_{12}$ from animal tissues or products (i.e., milk, butter, cheese, eggs, meat, poultry, etc.).

The absorption of vitamin $B_{12}$ in humans is complex. Vitamin $B_{12}$ in food is bound to proteins and is released from the proteins by the action of a high concentration of hydrochloric acid present in the stomach. This process results in the free form of the vitamin, which is immediately bound to a mixture of glycoproteins secreted by the stomach and salivary glands. These glycoproteins, called R-binders (or haptocorrins), protect vitamin $B_{12}$ from chemical denaturation in the stomach. The stomach's parietal cells, which secrete hydrochloric acid, also secrete a glycoprotein called intrinsic factor. Intrinsic factor binds vitamin $B_{12}$ and ultimately enables its active absorption. Although the formation of the vitamin $B_{12}$-intrinsic factor complex was initially thought to happen in the stomach, it is now clear that this is not the case. At an acidic pH the affinity of the intrinsic factor for vitamin $B_{12}$ is low whereas its affinity for the R-binders is high. When the contents of the stomach enter the duodenum, the R-binders become partly digested by the pancreatic proteases, which cause them to release their vitamin $B_{12}$. Because the pH in the duodenum is more neutral than that in the stomach, the intrinsic factor has a high binding affinity to vitamin $B_{12}$, and it quickly binds the vitamin as it is released from the R-binders. The vitamin $B_{12}$-intrinsic factor complex then proceeds to the lower end of the small intestine, where it is absorbed by phagocytosis by a specific distal ileal receptor, cubilin.

Epidemiological studies show a prevalence of B12 deficiency of around 20% (between 5% and 60%, depending on the definition of B12 deficiency used in the study) in the general population of industrialized countries. In the Framingham Offspring study, 39% of the US population was found to have subclinical B12 deficiency. The prevalence of B12 deficiency is as high as 75% in the Indian population because of the vegan diet or near vegan diet followed by most of the adherents of Hindi. Other groups who are at a higher risk of cobalamin deficiency are the elderly who have a high frequency of diminished gastric acid, needed to cleave cobalamin from the food source protein (Food Cobalamin Malabsorption), individuals using antacids, Proton Pump Inhibitors (PPIs), Histamine 2 (H2) blockers as well as diabetic patients who are treated with metformin. Also, people who undergo resection of the greater curve of their stomachs in Bariatric surgery are rendered B12 deficient by virtue of the removal of the synthetic site of Intrinsic Factor (IF).

Hence, the recognition that cobalamin deficiency is much more common than previously appreciated and that the role it occupies at the crossroads of the methionine cycle. A cobalamin deficiency will not only reduce the methylation of homocysteine to methionine and perpetuate the adequacy of S-adenosylmethionine (SAM), the methyl donor for many biological methylation reactions, it will also trap methylated folate and deny it a role in a multitude of metabolic and protein synthetic reactions. Furthermore, it will shift the onus of methylation of methionine to betaine and thereby diminish the amount of choline needed to synthesize phosphatidylcholine via the dominant CDP-choline synthetic cycle. This creates a choline deficiency, the implications of which are dire, particularly on the liver, where choline deficiency can lead to NAFLD and the sequelae associated with metabolic syndrome, diabetes, obesity, hyperlipidemia. Because of the folate fortification programs in many developed countries (like the US) and the high intake of vegetables in the diet, the prevalence of folate deficiency is not nearly as much of a problem as either cobalamin or choline, both of which are from animal source foods.

Accordingly, there remains a need in the art for improved methods to ensure full and adequate availability of these two key animal source essential food ingredients to negate the unintended consequence of B12 deficiency causing either an absolute or relative choline deficiency (in the liver) by forcing a disproportionate amount of choline to be channeled to one carbon methylation metabolism. Similarly, a choline deficiency that cannot meet its methylation obligations in the methionine cycle will more B12 to be dedicated to methylation of homocysteine and thereby reducing its availability for $B_{12}$-dependent enzyme methylmalonyl coenzyme A (CoA) mutase functions in the metabolism of propionate and certain of the amino acids, into succinyl CoA, for energy production in the cell.

Furthermore, subjects diagnosed with these diseases or conditions, or at risk for these diseases and conditions, still have the same dietary requirements for iron as healthy subjects and therefore, ensuring the adequacy of choline will reduce intracellular iron accumulation by increasing ferroportin expression and/or reduce the negative effects associated with intracellular iron accumulation.

The RDA for cobalamin is 2.4 ug/day, which is about how much the B12-IF receptor can absorb over about a 5 or 6 hour time period. With the significant number of conditions that contribute to the deficiency or absence of IF, it is no wonder that when faced with a severe B12 deficiency caused by the presence of autoantibodies to IF or the parietal cells in the stomach that make them, doctors are advised to only use injections of cobalamin, because oral absorption is not reliable if one cannot guarantee the adequate presence of IF. That notwithstanding, in recent years, oral vitamin B12 products have come on the market with doses of 500 ug-5000 ug, which are vastly more than the body can absorb or utilize. It has been demonstrated that 1 or less of these mega doses are being absorbed and it has been thought that the 99% of the administered dose remaining in the GI tract is benign and even the excess B12 absorbed into the circulation is benign.

Neither of these two assumptions is true as it has been demonstrated that excess B12 within the GI are utilized by the colonic bacteria, many of which have an ability to cleave off bits of the large B12 molecule and generate large amounts of B12 fragments, called analogues. These analogues contribute to the virulence of the microbial flora of the bowel and may lead to overgrowth syndromes like Irritable Bowel Syndrome and at the very least, an alteration in the gut microbiome, which can have implications on a variety of medical conditions. The gut microbiome integrates many important pathways, including those related to enterohepatic circulation of bile, cholesterol and phospholipids. The gut flora modulates host immunity, glucose, lipid, and energy metabolism, and choline availability, all of which play a role in NAFLD.

Furthermore, these microbial generated B12 analogues get absorbed and some of them have been shown to actually interfere with the co-factor role of B12 intracellularly, thereby creating a functional B12 deficiency for one carbon metabolism. In addition, an excess B12 absorption by diffusion from these massive oral B12 doses can raise the blood levels above 600 pmol/L, a level above which has been associated with a significant increase in malignancies—particularly hematological, smoking and alcohol related cancers. Therefore, there are significant reasons to ensure that very large doses of B12 are not administered to offset the confirmed or suspected absence or deficiency of Intrinsic Factor, as this practice has several very significant unintended negative consequences. The only way to ensure adequate oral intake of B12 is to administer a dose of B12 along with Intrinsic Factor to ensure an appropriate receptor mediated (and modulated) absorption without bathing the gut microflora in a growth promoting excess of B12. Normal absorption of B12-IF assumes no pathology to the distal ileum, where the B12-IF receptors reside, like Crohns disease or similar conditions.

Accordingly, there remains in the art a composition capable of delivering Intrinsic Factor to be able to bind to the appropriate amount of B12 contained in the diet or appropriate supplemental physiologic doses and deliver said B12 to the B12-IF receptors in the distal ileum for absorption of physiologic amounts of B12 to ensure tissue and cellular adequacy to complement and optimize the simultaneous administration of choline to optimize the efficacy of these two key and essential methyl donors.

SUMMARY OF THE INVENTION

One aspect of the invention encompasses a single dosage form composition. The single dosage form composition comprises (a) intrinsic factor in an amount of about 35 µg to about 10,000 µg; and (b) choline in a form of one or more physiologically acceptable salts, phospholipid bound forms, intermediates or derivatives thereof, and in a total amount of choline that is at least 5 mg to about 5000 mg. The composition may further comprises iron in a form of one or more physiologically acceptable iron compounds, chelates, complexes, or admixtures, and in a total elemental iron amount of about 5 mg to about 150 mg.

Another aspect of the invention encompasses a method for preventing a complication of pregnancy in a prenatal human subject or a human subject trying to conceive. The method comprises administering to the subject a single dosage form composition comprising (a) intrinsic factor in an amount of about 35 µg to about 10,000 µg; and (b) choline in a form of one or more physiologically acceptable salts, phospholipid bound forms, intermediates or derivatives thereof, and in a total amount of choline of at least 5 mg to about 5000 mg. Alternatively, the method comprises administering to the subject a single dosage form composition comprising (a) iron in a form of one or more physiologically acceptable iron compounds, chelates, complexes, or admixtures, and in a total elemental iron amount of about 30 mg to about 150 mg; and (b) choline in a form of one or more physiologically acceptable salts, phospholipid bound forms, intermediates or derivatives thereof, and in a total amount of choline of at least 125 mg to about 5000 mg.

Still another aspect of the invention encompasses a method for supplementing iron to a human subject. The method comprises administering to the subject a single dosage form composition comprising (a) iron in a form of one or more physiologically acceptable iron compounds, chelates, complexes, or admixtures, and in a total elemental iron amount of about 10 mg to about 150 mg; and (b) choline in a form of one or more physiologically acceptable salts, phospholipid bound forms, intermediates or derivatives thereof, and in a total amount of choline of at least 50 mg to about 5000 mg, wherein the subject has (i) iron deficiency and (ii) either an increased risk for, or is diagnosed with, non-alcoholic fatty liver disease, metabolic syndrome, or type 2 diabetes mellitus.

Yet another aspect of the invention encompasses a method for reducing intracellular iron accumulation and/or reducing the negative effects associated with intracellular iron accumulation. The method comprises administering to the subject a single dosage form composition comprising (a) intrinsic factor in an amount of about 35 µg to about 10,000 µg; and (b) choline in a form of one or more physiologically acceptable salts, phospholipid bound forms, intermediates or derivatives thereof, and in a total amount of choline of at least 5 mg to about 5000 mg, wherein the subject has a diagnosis of iron overload.

Yet still another aspect of the invention encompasses a method of for mitigating the risk for metabolic, cardiovascular and hepatic diseases in a human subject with Dysmetabolic Iron Overload Syndrome (DIOS). The method comprises orally administering an amount of choline in a form of one more physiologically acceptable salt in a total amount of about 5 mg to about 5000 mg. Alternatively, the method comprises administering to the subject a single dosage form composition comprising (a) intrinsic factor in an amount of about 35 µg to about 10,000 µg; and (b) choline in a form of one or more physiologically acceptable salts, phospholipid bound forms, intermediates or derivatives thereof, and in a total amount of choline of at least 5 mg to about 5000 mg.

A different aspect of the invention encompasses a method for reducing the risk of non-alcoholic fatty liver disease in a human subject receiving supplemental iron in a total elemental iron amount of about 20 mg to about 150 mg per day. The method comprises orally administering an amount of choline in a form of one more physiologically acceptable salt in a total amount of about 5 mg to about 5000 mg.

Still a different aspect of the inventions encompasses a method for reducing the risk of non-alcoholic fatty liver disease, or improving a sign or symptom of non-alcoholic fatty liver disease, in a human subject. The method comprises administering to the subject a single dosage form composition comprising (a) intrinsic factor in an amount of about 35 µg to about 10,000 µg; and (b) choline in a form of one or more physiologically acceptable salts, phospholipid bound forms, intermediates or derivatives thereof, and in a total amount of choline of at least 5 mg to about 5000 mg.

Other features and aspects of the invention are described in more detail herein.

DETAILED DESCRIPTION OF THE INVENTION

The present disclosure provides novel compositions comprising choline and intrinsic factor. The intrinsic factor of the compositions disclosed herein increases the absorption of vitamin B12 (either from the diet or optionally included in the composition), thereby concomitantly decreasing the reliance on betaine as a methyl donor and increasing the relative availability of choline to other metabolic fates, particularly in the liver. For example, choline deficiency has been shown to reduce the number of ferroportin transporters in the membrane wall of the liver cell. Accordingly, the present disclosure also provides a novel approach to reduce iron overload associated with or caused by intracellular iron accumulation and/or reduce the negative effects associated with intracellular iron accumulation or iron overload by administering to a subject in need thereof a single dosage form composition of the disclosure. Single dosage form compositions of this disclosure, as well as their intended uses, are described in further detail below.

I. Single Dosage Form Composition

One aspect of the disclosure is a single dosage form composition. As used herein, the term "single dosage form composition" refers to the amounts and types of components comprising a single dosage form. The term "dosage form" refers to a formulation of the components in physical form designed to allow the accurate and efficient administration to a subject, preferably to a human. Suitable dosage forms are those that are orally administered. Non-limiting examples of suitable dosage forms include capsules, tablets, pills, lozenges, soluble films, elixirs, syrups, solutions, suspensions, emulsions, semisolids and gels. Capsules may be a one-piece or two-piece capsule, and have a soft or hard shell. Non-limiting examples of tablets include a suspension tablet, a chewable tablet, an effervescent tablet, and an orally disintegrating tablet. Semisolids may include, but are not limited to, gel-filled chews and gelatinous chews.

An aspect of the disclosure is a single dosage form composition comprising choline in combination with intrinsic factor. Single dosage form compositions containing choline in combination with intrinsic factor may further comprise iron, vitamins, minerals, amino acids, and trace elements. A single dosage form composition comprising choline in combination with intrinsic factor can be advantageous for subjects with choline deficiency and/or vitamin B12 deficiency. For example, a single dosage form composition comprising choline in combination with intrinsic factor can be advantageous for subjects with NAFLD, or with the sequelae associated with metabolic syndrome, diabetes, obesity, hyperlipidemia. A single dosage form composition comprising choline in combination with intrinsic factor can also be advantageous for subjects at risk of, or diagnosed with a disease or condition associated with iron overload.

Another aspect of the disclosure is a single dosage form composition comprising choline in combination with iron. Supplemental iron, in particular high doses of supplemental iron of about 30 mg/day or more, may cause gastrointestinal side effects, such as nausea and constipation. A single dosage form composition of the disclosure may mitigate one or more gastrointestinal side effects of unabsorbed iron and improve bioavailability of iron by inclusion of choline, which is described in detail below. A single dosage form composition comprising choline in combination with iron is also advantageous for subjects that are in need of iron supplementation but are predisposed to, at risk of, or diagnosed with a disease or condition associated with iron overload. Non-limiting examples of disease and conditions associated with iron overload include hepatocellular carcinogenesis, colonic neoplasia, colorectal carcinogenesis, fatty liver disease, nonalcoholic steatohepatitis, insulin resistance, type I and type II diabetes, atherosclerosis, and dysmetabolic iron overload syndrome. Single dosage form compositions containing choline in combination with iron may further comprise intrinsic factor, vitamins, minerals, amino acids, and trace elements.

(a) Choline

A single dosage form composition of the disclosure comprises choline in a form of one or more physiologically acceptable salts, phospholipid bound forms, intermediates or derivatives thereof, and in an amount that provides at least 5 mg to about 5000 mg of choline. Calculation of suitable amounts of choline salts, phospholipid bound forms, intermediates of choline and derivatives of choline to provide at least 55 mg to about 5000 mg of choline is well within the level of one of ordinary skill in the art. The adequate intake (AI) for choline for a male human subject age 19+ years is 550 mg per day. The AI for choline for a female human subject age 19+ years is 425 mg per day, with an amount of 450 mg per day during pregnancy and 550 mg per day during lactation.

Accordingly, a single dosage form composition may comprise a choline amount of about 5 mg to about 4000 mg, about 5 mg to about 3500 mg, about 5 mg to about 3000 mg, about 5 mg to about 2500 mg, about 5 mg to about 2000 mg, about 5 mg to about 1500 mg, about 5 mg to about 1000 mg, about 5 mg to about 500 mg, or about 5 mg to about 250 mg. Further, a single dosage form composition may comprise a choline amount of about 15 mg to about 4000 mg, about 15 mg to about 3500 mg, about 15 mg to about 3000 mg, about 15 mg to about 2500 mg, about 15 mg to about 2000 mg, about 15 mg to about 1500 mg, about 15 mg to about 1000 mg, about 15 mg to about 500 mg, or about 15 mg to about 250 mg. Still further, a single dosage form composition may comprise a choline amount of about 25 mg to about 4000 mg, about 25 mg to about 3500 mg, about 25 mg to about 3000 mg, about 25 mg to about 2500 mg, about 25 mg to about 2000 mg, about 25 mg to about 1500 mg, about 25 mg to about 1000 mg, about 25 mg to about 500 mg, or about 25 mg to about 250 mg. Alternatively, a single dosage form composition may comprise a choline amount of about 55 mg to about 4000 mg, about 55 mg to about 3500 mg, about 55 mg to about 3000 mg, about 55 mg to about 2500 mg, about 55 mg to about 2000 mg, about 55 mg to about 1500 mg, about 55 mg to about 1000 mg, about 55 mg to about 500 mg, or about 55 mg to about 250 mg. Further, a single dosage form composition may comprise a choline amount of about 75 mg to about 4000 mg, about 75 mg to about 3500 mg, about 75 mg to about 3000 mg, about 75 mg to about 2500 mg, about 75 mg to about 2000 mg, about 75 mg to about 1500 mg, about 75 mg to about 1000 mg, about 75 mg to about 500 mg, or about 75 mg to about 250 mg. In addition, a single dosage form composition may comprise a choline amount of about 125 mg to about 4000 mg, about 125 mg to about 3500 mg, about 125 mg to about 3000 mg, about 125 mg to about 2500 mg, about 125 mg to about 2000 mg, about 125 mg to about 1500 mg, about 125 mg to about 1000 mg, about 125 mg to about 500 mg, or about 125 mg to about 250 mg. A single dosage form composition may also comprise a choline amount of about 200 mg to about 4000 mg, about 200 mg to about 3500 mg, about 200 mg to about 3000 mg, about 200 mg to about 2500 mg, about 200 mg to about 2000 mg, about 200 mg to about 1500 mg, about 200 mg to about 1000 mg, about 200 mg to about 500 mg, or about 200 mg to about 250 mg.

Choline (hydroxyethyl trimethyl ammonium hydroxide) is considered to be a vitamin of the B complex and is derivable from many foods. The term choline, as used herein, refers not only to the isolated choline molecule (i.e., free choline), but also to any biologically compatible salt of choline (e.g., choline bitartrate), phospholipid bound choline, and choline precursors and choline metabolites, wherein the choline precursors or choline metabolites are capable of being converted into choline. The salt of choline comprises the chemical formula $(CH_3)_3N^+(CH_2)_2OHX^-$, wherein $X^-$ is a negative counter ion. Non-limiting examples of choline salts include choline bitartrate, choline chloride, choline dihydrogen citrate, choline salicylate, choline phosphate, choline bicarbonate, and choline magnesium trisalicylate. Specifically, a single dosage form composition of the disclosure may comprise choline bitartrate, choline dihydrogen citrate, or choline chloride. Preferably, the choline salt has a choline cation concentration that is greater than 40% by weight, greater than 50% by weight, greater than 60% by weight, greater than 70% by weight, greater than 75% by weight, or greater than 80% by weight. Alternatively, the form of choline used in a single dosage form composition of the disclosure may comprise a phospholipid bound choline including, but not limited to, phosphatidylcholine and soy lecithin. In addition, choline precursors and choline metabolites such as CDP-choline (also known as citicoline, cytidine diphosphate-choline or cytidine 5'-diphosphocholine) may be used in a single dosage form composition of the disclosure.

In a particular embodiment, choline is present in the form of choline bitartrate. Bitartrate contains two chiral carbons. Accordingly, bitartrate may be DL-choline bitartrate, D-choline bitartrate or L-choline bitartrate. In the D- and L-forms, both chiral carbons are either D or L, respectively. In certain embodiments, the choline bitartrate is L-choline bitartrate. Accordingly, the L-choline bitartrate is optically active to plane polarizing light. More specifically, the L-choline bitartrate rotates plane polarized light more than +17.5 degrees. Only L-choline bitartrate is in the USP monograph. As L-amino acids are generally found in nature, the L-form of choline bitartrate may also be referred to as the natural form of choline bitartrate. In other embodiment, the choline bitartrate is a racemic mixture of D-choline bitartrate, L-choline bitartrate or DL-choline bitartrate. Accordingly, the racemic mixture is optically inactive to plane polarizing light. More specifically, the racemic mixture rotates plane polarized light less than +17.5 degrees.

In another particular embodiment, choline is present in the form of choline chloride as a product that (a) contains a choline cation concentration that is at least about 60% by weight, at least about 70% by weight, or at least about 75% by weight, (b) has a moisture content below 2.5%, preferably about 1%, more preferably about 0.5%, and (c) is substantially free of organic solvent (e.g. the wt % of the solvent is ≤25%, preferably ≤20%, more ≤15%, even more preferably ≤10%). Although all choline chloride is the same at the molecular level, there are quantifiable differences between commercially available choline chloride products. For example, a choline chloride product may contain chloride salts (e.g. KCl, $MgCl_2$, $NH_4Cl$, etc.) in addition to choline chloride. As a result, tests that confirm choline chloride content by assuming a 1:1 ratio between choline content and chloride content and quantifying the chloride content will overestimate the choline content due to the presence of excess chloride ions. For accurate confirmation of choline chloride content, the Reinecke salt test is often recommended with ion chromatography as a final confirmation. Both offer high levels of accuracy and precisely identify any product adulteration. The choice of manufacturing process may also result in measurable differences in a choline chloride product such as varying amounts of residual total trimethylaminesammonium, dioxin content, and moisture content. In an exemplary embodiment, choline is present in the form of choline chloride, for example as the product Vitacholine™.

(b) Intrinsic Factor

A single dosage form composition of the disclosure comprises intrinsic factor in an amount of about 35 μg to about 10,000 μg. Intrinsic factor (IF) is a glycosylated protein that is secreted from the gastric mucosa and the pancreas. For example, a single dosage form composition may comprise an amount of intrinsic factor of about 35 μg to about 10,000 μg, about 35 μg to about 5,000 μg, about 35 μg to about 1,000 μg, or about 35 μg to about 500 μg. Alternatively, a single dosage form composition may comprise an amount of intrinsic factor of about 35 μg to about 250 μg, about 35 μg to about 350 μg, about 150 μg to about 450 μg, about 350 μg to about 650 μg, about 500 μg to about 800 μg, about 650 μg to about 950 μg. A single dosage form composition may also comprise an amount of intrinsic factor of about 1,000 μg to about 2,000 μg, about 1,500 μg to about 2,500 μg, about 2,000 μg to about 3,000 μg, about 2,500 μg to about 3,500 μg, about 3,000 μg to about 4,000 μg, about 3,500 μg to about 4,500 μg, about 4,000 μg to about 5,000 μg, about 4,500 μg to about 5,500 μg, about 5,000 μg to about 6,000 μg, about 5,500 μg to about 6,500 μg, about 6,000 μg to about 7,000 μg, about 6,500 μg to about 7,500 μg, about 7,000 μg to about 8,000 μg, about 7,500 μg to about 8,500 μg, about 8,000 μg to about 9,000 μg, about 8,500 μg to about 9,500 μg, about 9,000 μg to about 10,000 μg, or about 9,500 μg to about 10,000 μg.

In some embodiments, the intrinsic factor is recombinant human intrinsic factor (rhIF). rHIF can be derived from a mammalian cell or a plant cell. In still other embodiments, the intrinsic factor and vitamin $B_{12}$ are included as rhIF-$B_{12}$ complexes. IF binds $B_{12}$ with picomolar affinity ($K_d$~1 μM), such that about 36 μg of IF binds to about 1 μg of vitamin B12. Accordingly, one of skill in the art will be able to calculate the amount of vitamin B12 provided as an rhIF-$B_{12}$ complex based on the amount of IF included in the composition. Exemplary recombinant IF is disclosed in U.S. application Ser. No. 10/483,849, filed Jul. 12, 2002 and PCT Application No. PCT/US2014/038220, each of which are incorporated herein by reference. Exemplary recombinant IF-$B_{12}$ complexes are disclosed in PCT Application No. PCT/US2014/052381, the entirety of which is incorporated herein by reference.

(c) Iron

Entrapment of iron within the cell, whether it be the enterocyte, colonic epithelium, hepatic parenchyma or macrophages, can lead to iron overload. Iron overload is an excess (too much) iron in the body. Excess iron in vital organs, even in mild cases of iron overload, increases the risk for liver disease (NAFLD, cirrhosis, hepatocellular carcinogenesis), colonic neoplasia, colorectal carcinogenesis, atherosclerosis, heart attack or heart failure, insulin resistance, diabetes mellitus, osteoarthritis, osteoporosis, metabolic syndrome, hypothyroidism, hypogonadism, and hypopituitarism, numerous symptoms and in some cases premature death. Iron mismanagement resulting in overload can accelerate such neurodegenerative diseases as Alzheimer's, early-onset Parkinson's, Huntington's, epilepsy and multiple sclerosis. Iron overload can be inherited (genetic) or acquired by receiving numerous blood transfusions, getting iron shots or injections, or consuming high levels of supplemental iron. Non-limiting examples of signs and symptoms of iron overload include chronic fatigue, joint pain, abdominal pain, irregular heart rhythm, skin color changes (bronze, ashen-gray green), loss of period, loss of interest in sex, hair loss, enlarged liver or spleen, impotence, infertility, depression, adrenal function problems, early onset neurodegenerative disease, elevated blood sugar, elevated liver enzymes, and elevated iron (serum iron, serum ferritin).

A single dosage form composition of the disclosure comprises iron in a form of one or more physiologically acceptable iron compounds, chelates, complexes, or admixtures, and in a total elemental iron amount of about 5 mg to about 500 mg. For example, a single dosage form composition may comprise a total element iron amount of about 5 mg to about 500 mg, about 10 mg to about 500 mg, about 15 mg to about 500 mg, about 20 mg to about 500 mg, about 25 mg to about 500 mg, about 5 mg to about 400 mg, about 5 mg to about 300 mg, about 5 mg to about 200 mg, about 5 mg to about 100 mg, about 5 mg to about 50 mg, about 10 mg to about 400 mg, about 10 mg to about 300 mg, about 10 mg to about 200 mg, about 10 mg to about 100 mg, about 10 mg to about 50 mg, about 20 mg to about 400 mg, about 20 mg to about 300 mg, about 20 mg to about 200 mg, about 20 mg to about 100 mg, or about 20 mg to about 50 mg. Alternatively, a single dosage form composition may comprise a total element iron amount of about 30 mg to about 500 mg, about 30 mg to about 400 mg, about 30 mg to about 300 mg, about 30 mg to about 200 mg, about 30 mg to about 100 mg, or about 30 mg to about 50 mg. Further, a single dosage form composition may comprise a total elemental iron amount of about 40 mg to about 500 mg. In another aspect, a single dosage form composition may comprise a total elemental iron amount of about 50 mg to about 500 mg. Additionally, a single dosage form composition may comprise a total element iron amount of about 35 mg to about 500 mg, about 45 mg to about 500 mg, about 55 mg to about 500 mg, about 60 mg to about 500 mg, about 65 mg to about 500 mg, about 70 mg to about 500 mg, about 75 mg to about 500 mg, or about 80 mg to about 500 mg. Further, a single dosage form composition may comprise a total element iron amount of about 40 mg to about 400 mg, about 40 mg to about 300 mg, about 40 mg to about 200 mg, about 40 mg to about 100 mg, about 50 mg to about 400 mg, about 50 mg to about 300 mg, about 50 mg to about 200 mg, or about 50 mg to about 100 mg.

Physiologically acceptable grades of elemental iron that can be used in a single dosage from composition of the disclosure include without limitation elemental iron, iron compounds in the form of a salt (soluble, slightly soluble, or insoluble), chelated iron (specifically, chelated to an amino acid), iron complexes, non-reactive iron such as carbonyl iron and reduced iron, and combinations thereof.

Non-limiting examples of suitable soluble iron salts include ferric hypophosphite, ferric albuminate, ferric chloride, ferric citrate, ferric oxide saccharate, ferric ammonium citrate, ferrous chloride, ferrous gluconate, ferrous iodide, ferrous sulfate, ferrous lactate, ferrous fumarate, heme, ferric trisglycinate, ferrous bisglycinate, ferrous asparto glycinate, ferric nitrate, ferrous hydroxide saccharate, ferric sulfate, ferric gluconate, ferric aspartate, ferrous sulfate heptahydrate, ferrous phosphate, ferric ascorbate, ferrous formate, ferrous acetate, ferrous malate, ferrous glutamate, ferroglycine sulfate, ferric oxide hydrate, ferric pyrophosphate soluble, ferric hydroxide saccharate, ferric manganese saccharate, ferric subsulfate, ferric ammonium sulfate, ferrous ammonium sulfate, ferric sesquichloride, ferric manganese citrate, ferric quinine citrate, ferric sodium citrate, ferric sodium edetate, ferric formate, ferric ammonium oxalate, ferric potassium oxalate, ferric sodium oxalate, ferric peptonate, ferric manganese peptonate, other pharmaceutically acceptable iron salts, and combinations thereof.

Non-limiting examples of suitable slightly soluble iron salts include ferric acetate, ferric fluoride, ferric phosphate, ferric pyrophosphate, ferrous pyrophosphate, ferrous carbonate saccharated, ferrous carbonate mass, ferrous succinate, ferrous citrate, ferrous tartrate, ferric fumarate, ferric succinate, ferrous hydroxide, ferrous nitrate, ferrous carbonate, ferric sodium pyrophosphate, ferric tartrate, ferric potassium tartrate, ferric subcarbonate, ferric glycerophosphate, ferric saccharate, ferric hydroxide saccharate, ferric manganese saccharate, ferrous ammonium sulfate, other pharmaceutically acceptable iron salts, and combinations thereof.

Non-limiting examples of suitable insoluble iron salts include ferric sodium pyrophosphate, ferrous carbonate, ferric hydroxide, ferrous oxide, ferric oxyhydroxide, ferrous oxalate, other pharmaceutically acceptable iron salts and combinations thereof.

Exemplary chelated iron complexes are disclosed in U.S. Pat. Nos. 4,599,152, 4,830,716, 6,716,814, and 8,007,846, each of which are incorporated herein by reference.

Non-limiting examples of suitable iron complexes include polysaccharide-iron complex, methylidine-iron complex, ethylenediaminetetraacetic acid (EDTA)-iron complex, phenanthrolene iron complex, p-toluidine iron complex, ferrous saccharate complex, ferrlecit, ferrous gluconate complex, ferrum *vitis*, ferrous hydroxide saccharate complex, iron-arene sandwich complexes, acetylacetone iron complex salt, iron-dextran complex, iron-dextrin complex, iron-sorbitol-citric acid complex, saccharated iron oxide, ferrous fumarate complex, iron porphyrin complex, iron phtalocyamine complex, iron cyclam complex, dithiocarboxy-iron complex, desferrioxamine-iron complex, bleomycin-iron complex, ferrozine-iron complex, iron perhaloporphyrin complex, alkylenediamine-N,N-disuccinic acid iron (III) complex, hydroxypyridone-iron(III) complex, aminoglycoside-iron complex, transferrin-iron complex, iron thiocyanate complex, iron complex cyanides, porphyrinato iron(III) complex, polyaminopolycarbonate iron complexes, dithiocarbamate iron complex, adriamycin iron complex, anthracycline-iron complex, N-methyl-D-glucamine dithiocarbamate (MGD)-iron complex, ferrioxamine B, ferrous citrate complex, ferrous sulfate complex, ferric gluconate complex, ferrous succinate complex, polyglucopyranosyl iron complex, polyaminodisuccinic acid iron complex, biliverdin-iron complex, deferiprone iron complex, ferric oxyhydride-dextran complex, dinitrosyl dithiolato iron complex, iron lactoferrin complexes, 1,3-ethylenediaminetetraacetic acid (EDTA) ferric complex salts, diethylenetriaminepentaacetic acid iron complex salts, cyclohexanediaminetetraacetic acid iron complex salts, methyliminodiacetic acid iron complex salts, glycol ether diaminetetraacetic acid iron complex salts, ferric hydroxypyrone complexes, ferric succinate complex, ferric chloride complex, ferric glycine sulfate complex, ferric aspartate complex, sodium ferrous gluconate complex, ferrous hydroxide polymaltose complex, other pharmaceutically acceptable iron complexes and combinations thereof.

In an aspect, the elemental iron used in a single dosage form composition of the disclosure is an iron amino acid chelate. For example, amino acid chelates are becoming well accepted as a means of increasing the metal content in biological tissues of man, animals and plants. Amino acid chelates are products resulting from the reaction of a polypeptide, dipeptide or naturally occurring alpha amino acid with a metal ion having a valence of two or more. The alpha amino acid and metal ion form a ring structure wherein the positive electrical charges of the metal ion are neutralized by the electrons of the carboxylate or free amino groups of the alpha amino acid. Although the term amino acid as used herein refers only to products obtainable through protein hydrolysis, synthetically produced amino acids are not to be excluded provided they are the same as those obtained through protein hydrolysis. Accordingly, protein hydrolysates such as polypeptides, dipeptides and naturally occurring alpha amino acids are collectively referred to as amino acids. Additional suitable amino acid chelates include for example but are not limited to ethylenediaminetetraacetic acid (EDTA), monohydroxyethylethylenediaminetriacetic acid, diethylenetriaminepentaacetic acid, monohydroxyethyldiglycine and dihydroxyethylglycine. Additional examples of mixed amino acid chelates of iron are described in U.S. Pat. No. 8,007,846, the entirety of which is incorporated herein by reference. Specific examples of iron amino acid chelates include ferrous aspartate, ferrous asparto glycinate, ferrous bisglycinate and ferrous histidinate. Specifically, the iron amino acid chelate may be ferrous asparto glycinate or ferrous bisglycinate.

Alternatively, the elemental iron used in a single dosage form composition of the disclosure is in the ferric form. Specific examples of ferric iron include ferric oxide-hydroxide, ferric acetate, ferric bromide, ferric chloride, ferric chromate, ferric citrate, ferric ammonium citrate, ferric fluoride, ferric hydroxide, ferric nitrate, ferric polymaltose, ferric phosphate, ferric pyrophosphate, ferric oxalate, ferric ammonium oxalate, ferric sulfate, ferroglycine sulfate, ferric sulfide, ferric glycinate (Iron Taste-Free® of Albion Laboratories, Inc. or a product technically equivalent thereto) and EDTA ferric sodium salt. Specifically, the iron is ferric glycinate.

In a particular embodiment, iron is present in the form of ferrous asparto glycinate, for example as the product Sumalate® of Albion Laboratories, Inc. or a product technically equivalent thereto. In another particular embodiment, iron is present in the form of ferrous bisglycinate, for example as the product Ferrochel® of Albion Laboratories, Inc. or a product technically equivalent thereto. In yet another embodiment, iron is present in the form of ferric glycinate, for example as the product Iron Taste-Free® of Albion Laboratories, Inc. or a product technically equivalent thereto.

Admixtures of two or more of the above iron grades, compounds and complexes can be used if desired. In a particular embodiment, any of the single dosage forms provided herein may have both ferrous asparto glycinate (Sumalate®) and ferrous bisglycinate (Ferrochel®) present in a total elemental iron amount of about 30 mg to about 500 mg, for example about 40 mg to about 500 mg, or about 50 mg to about 500 mg. In another particular embodiment, any of the single dosage forms provided herein may have ferric glycinate (Iron Taste-Free®) combined with either ferrous asparto glycinate (Sumalate®) or ferrous bisglycinate (Ferrochel®) or both present in a total elemental iron amount of about 30 mg to about 500 mg, for example about 40 mg to about 500 mg, or about 50 mg to about 500 mg.

The different forms of iron contain varying amounts of elemental iron. For example, ferrous fumarate is 33% elemental iron by weight, whereas ferrous sulfate is 20% and ferrous gluconate is 12% elemental iron. A skilled artisan would be able to determine the amount of elemental iron present in the different forms of iron.

(d) Optional Components

A single dosage form composition of the disclosure can optionally contain additional components. For example, a single dosage form composition of the disclosure may further comprise one or more additional minerals, vitamins, fatty acids, amino acids, or combinations thereof. In addition, a single dosage form composition of the disclosure may further comprise one or more pharmaceutically acceptable excipient, such as those that are conventionally used in preparing pharmaceutical formulations.

Non-limiting examples of minerals that may be included as an optional component include calcium (about 10 mg to about 400 mg), chromium (about 3.75 µg to about 150 µg), copper (about 1 mg to about 30 mg), magnesium (about 5 mg to about 100 mg), manganese (about 1.5 mg to about 60 mg), molybdenum (about 0.5 to about 3 mg), potassium (about 3.75 mg to about 150 mg), iodine (about 37.5 µg to about 1500 µg), selenium (about 2.5 µg to about 100 µg), vanadium (about 1 µg to about 100 mg) and zinc (about 5 mg to about 100 mg) in the form of salts and/or complexes of these elements. The minerals may be included in any form that has at least some bioavailability to the subject, and may be present in a single form or may be present as a mixtures of two or more forms. Illustrative bioavailable forms include, but are not limited to, calcium carbonate, monocalcium phosphate, dicalcium phosphate, hydroxyapatite (including microcrystalline hydroxyapatite), calcium citrate tetrahydrate, calcium citrate malate, calcium formate, calcium gluconate, calcium glycerophosphate, calcium bisglycinate, calcium lactate, calcium levulinate, dicalcium malate (for example DimaCal® of Albion Laboratories, Inc. and products technically equivalent thereto), calcium succinate, calcium tartrate, magnesium aspartate, magnesium creatine chelate, magnesium glycinate, magnesium glycyl glutamine chelate, magnesium lysyl glycinate, dimagnesium malate, chromium nicotinate glycinate, copper glycinate, manganese glycinate, molybdenum glycinate, selenomethionine, sodium selenite, sodium selenite, sodium-enriched yeast or yeast extract, vanadium nicotinate glycinate, zinc oxide, zinc sulfate, zinc amino acid chelates (e.g., zinc arginate, zinc aspartate, zinc bisglycinate, citrated zinc bisglycinate and zinc histidinate), zinc acetate, zinc acetate dihydrate, zinc ascorbate, zinc citrate, zinc gluconate, zinc ketoglutarate, zinc malate, zinc picolinate, zinc stearate and zinc succinate.

Non-limiting examples of vitamins that may be included as an optional component include vitamin A (about 1,000 IU to about 250,000 IU), vitamin B, vitamin B1 (about 25 mg to about 1000 mg), vitamin B2 (about 25 mg to about 1000 mg), vitamin B3 (about 7 mg to about 23 mg), vitamin B5 (about 25 mg to about 75 mg), vitamin B6 (about 1 mg to about 1000 mg), vitamin B7 (about 25 µg to about 1000 µg), vitamin B9 (about 0.5 mg to about 2 mg), vitamin B12 (about 1 µg to about 1 mg), vitamin C (about 5 mg to about 3000 mg), vitamin D (about 100 IU to about 4000 IU), vitamin E (about 7.5 IU to about 1000 IU), vitamin K (about 1 µg to about 400 µg), inositol (about 25 mg to about 1000 mg), p-aminobenzoic acid (about 25 mg to about 1000 mg), folic acid (about 100 µg to about 4000 µg), and combinations thereof. As used herein, the term "vitamin" includes not only the vitamin, but also provitamins and derivatives thereof. "Provitamins" include compounds that may be converted into a vitamin in a subject, as by a metabolic process. Derivatives include chemically or otherwise modified vitamins that exhibit the same nutritional properties as the vitamin. For example, the term "vitamin D" includes not only cholecalciferol (vitamin $D_3$) but analogs, precursors, provitamins and metabolites thereof having vitamin D activity including without limitation ergocalciferol (vitamin $D_2$), 25-hydroxyergocalciferol, 25-hydroxycholecalciferol (25-OH vitamin D) and 1,25-dihydroxycholecalciferol (1,25-diOH vitamin D).

Non-limiting examples of fatty acids that may be included as an optional component include omega-3 (about 10 mg to about 1000 mg) and omega-6 (about 1 mg to about 100 mg) fatty acids.

Non-limiting examples of pharmaceutically acceptable excipients that may be included as an optional component include diluents, binding agents, dispersants, wetting agents, lubricants, glidants, etc. Many excipients have two or more functions in a pharmaceutical composition. Characterization herein of a particular excipient as having a certain function, e.g., diluent, binding agent, disintegrant, etc., should not be read as limiting to that function.

Suitable diluents may include, but are not limited to, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; magnesium carbonate; magnesium oxide; bentonite; kaolin; sodium chloride; and the like. A diluent may be present individually or in combination with one or more additional diluent.

Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC or hypromellose), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone), for example povidone K-15, K-30 and K-29/32; polyacrylic acids (carbomers); polymethacrylates; and the like.

Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like.

Suitable wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; sorbitan esters, for example sorbitan monolaurate, sorbitan monooleate, sorbitan monopalmitate and sorbitan monostearate; tyloxapol; and the like.

Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like.

Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates.

Other excipients such as buffering agents, stabilizers, antioxidants, antimicrobials, colorants, flavors and sweeteners are known in the pharmaceutical art and can be used. Tablets can be uncoated or can comprise a core that is coated, for example with a nonfunctional film or a release-modifying or enteric coating. Capsules can have hard or soft shells comprising, for example, gelatin and/or HPMC, optionally together with one or more plasticizers.

(e) Methods of Making a Single Dosage Form

A single dosage form composition of the disclosure can be prepared by any of the conventional processes of pharmacy well known to those of skill in the art. Generally speaking, the components of a single dosage form composition are combined into pellets, powders, beads and granules, which are then processed into dosage form.

A single dosage form in the form of a tablet may be produced using any suitable method known in the art. In one embodiment, components of a single dosage form composition according to this disclosure may be combined with the one or more excipients and granulated into tablet granules using any of the known granulation devices described previously. In this same embodiment, the tablet granules may be optionally blended with one or more additional excipients, including but not limited to lubricants. The resulting tablet blend may be compressed into a tablet form. In another embodiment, one or more excipients incorporated into the tablet granules may include a release-controlling polymer to impart a modified release profile to the resulting tablet. In yet another embodiment, one or more components of a single dosage form composition may be coated with a release-controlling polymer prior to incorporating the component(s) into a solid tablet form in order to impart a modified release profile to the resulting tablet. In an additional embodiment, the solid tablet form may be coated with a release-controlling polymer to impart a modified release profile.

A single dosage form in the form of a capsule may be produced using any suitable method known in the art including but not limited to direct loading into two-piece telescoping hard capsules. Non-limiting examples of suitable hard capsules include hard starch capsules, hard gelatin capsules, and hard cellulose capsules. In one embodiment, the capsule form of a single dosage form composition of this disclosure may be produced by loading the composition into the hard capsule and sealing the capsule. In other embodiments, one or more components of a single dosage form composition of this disclosure may be coated with a release-controlling polymer to impart a modified release profile to the hard capsule composition. In yet other embodiments, a fraction of the total amount of one or more components of a single dosage form composition of this disclosure may be coated with a release-controlling polymer and combined with the remaining uncoated fraction prior to loading into the hard capsule.

Other combinations of the embodiments described above may be used to produce additional embodiments having a desired release profile or other desired performance characteristic, including but not limited to masked taste, acceptable tongue-feel and mouth-feel, and enhanced stability.

II. Methods

In an aspect, the disclosure provides a method for preventing a complication of pregnancy in a prenatal human subject or a human subject trying to conceive. The method comprises administering to the subject a single dosage form composition comprising (a) intrinsic factor in an amount of about 35 µg to about 10,000 µg; and (b) choline in a form of one or more physiologically acceptable salts, phospholipid bound forms, intermediates or derivatives thereof, and in a total amount of choline that is at least 5 mg to about 5000 mg. The composition may further comprise iron in a form of one or more physiologically acceptable iron compounds, chelates, complexes, or admixtures, and in a total elemental iron amount of about 5 mg to about 150 mg. Various aspects of the composition are described in Section I.

Another aspect of the disclosure provides a method for preventing a complication of pregnancy in a prenatal human subject or a human subject trying to conceive. The method comprises administering to the subject a single dosage form composition comprising (a) iron in a form of one or more physiologically acceptable iron compounds, chelates, complexes, or admixtures, and in a total elemental iron amount of about 30 mg to about 150 mg; and (b) choline in a form of one or more physiologically acceptable salts, phospholipid bound forms, intermediates or derivatives thereof, and in a total amount of choline that is at least 125 mg to about 5000 mg. The composition may further comprise intrinsic factor in an amount of about 35 µg to about 10,000 µg. Various aspects of the composition are described in Section I.

Specifically, the complication of pregnancy may be development of non-alcoholic fatty liver disease in the subject, development of metabolic syndrome in the subject, development of neural tube defects in the fetus, or any combination thereof. As used herein, the term "preventing", "prevent" or "prevention" refers to stopping a disease or disorder form occurring, as well as alleviating, reducing, or mitigating one or more signs and/or symptoms associated with the disease or disorder. There is an increased need for choline during pregnancy to support optimal fetal brain development, placental function, and maternal liver function. A composition of the disclosure restores pregnancy-induced alterations in choline metabolism. Accordingly, a composition of the disclosure mitigates one or more of the signs and symptoms of non-alcoholic fatty liver disease, metabolic syndrome, neural tube defects in the fetus, orofacial cleft in the fetus, preeclampsia and/or pathological antecedents of preeclampsia. A composition of the disclosure also influences the development of the hippocampus and memory function in the fetus. A composition of the disclosure promotes optimal fetal outcomes (birth defects, brain development) and maternal liver and placental function.

Non-alcoholic fatty liver disease or NAFLD is the buildup of extra fat in liver cells that is not caused by alcohol. Specifically, if more than 5%-10% percent of the liver's weight is fat, then it is called a fatty liver (steatosis). NAFLD is histologically characterized by the presence of macrovesicular steatosis, and it occurs in the absence of excessive alcohol consumption. Its histologic spectrum includes simple steatosis and non-alcoholic steatohepatitis (NASH). The latter presentation can progress to cirrhosis in 15% to 20% of patients over the ensuing 10 to 15 years. A subject may have an increased risk for NAFLD. Non-limiting examples of risk factors for NAFLD include overweight, obesity, diabetes, high cholesterol, high triglycerides, rapid weight loss and/or poor eating habits. A subject may be diagnosed with NAFLD. Non-limiting examples of symptoms useful in the diagnosis of NAFLD include fatigue, weakness, weight loss, loss of appetite, nausea, abdominal pain, spider-like blood vessels, yellowing of the skin and eyes (jaundice), itching, fluid buildup and swelling of the legs (edema) and abdomen (ascites), and mental confusion. Blood tests to evaluate liver enzymes and/or an ultrasound may also be used to diagnose NAFLD.

Metabolic syndrome is a cluster of conditions including increased blood pressure, a high blood sugar level, excess body fat around the waist and abnormal cholesterol levels which increases risk of heart disease, stroke and diabetes. A subject may be at risk for metabolic syndrome. Non-limiting examples of risk factors for metabolic syndrome include age (risk increases with age, affecting 40% of people over the age of 60), race (Hispanics and Asians are at a greater risk), obesity, diabetes (gestational diabetes or family history of type 2 diabetes), and other diseases such as cardiovascular disease, nonalcoholic fatty liver disease or polycystic ovary syndrome. A subject may be diagnosed with metabolic syndrome. Non-limiting examples of symptoms useful in the diagnosis of metabolic syndrome include a large waist circumference, high blood sugar, and other symptoms of diabetes including increased thirst and urination, fatigue, and blurred vision. Additional methods for diagnosing metabolic syndrome include a large waist circumference (at least 35" for women and 40" for men), high triglyceride level (at least 150 mg per dL), reduced HDL cholesterol (less than 40 mg/dL in mean or less than 50 mg/dL in women), increased blood pressure (at least 130/85 mm Hg), and elevated fasting blood sugar (at least 100 mg/dL).

Insulin resistance (IR) is central to a cluster of frequent and increasingly prevalent pathologies, including type 2 diabetes mellitus, central obesity, hypertension hepatic steatosis, and dyslipidemia. IR contributes to major causes of morbidity and mortality worldwide. Epidemiological and genetic studies in human and animal models have demonstrated the importance of both genetic and environmental factors in the etiology of IR. Dietary variation and intervention, in particular, have a strong influence on the development of IR. Nonalcoholic fatty liver disease (NAFLD) is the most frequent liver condition associated with IR. It is associated with hepatic IR and characterized by hepatic accumulation of triglycerides, or steatosis. Although the causes of human NAFLD are not understood, it has been shown in animal models that choline-deficient diets are associated with NAFLD.

The critical involvement of the gut microbiota in biological processes controlling host metabolic regulations, including those involved in insulin sensitivity and caloric recovery from the diet, is emerging from recent studies. Conventionalized animals have 40% more body fat than germ-free animals. Moreover, diet is known to modulate gut-microbial composition, and obesity correlates with variation in the distribution of Bacteroidetes and Firmicutes in mice. Hence, symbiotic bacterial contributions to IR and NAFLD should not be overlooked. It has recently been shown that lower plasma PC levels in strain 129S6 on a high fed diet compared with BALB/c mice can be explained by reduced bioavailability of choline because of conversion of choline into methylamines by gut microbiota, with subsequent urinary excretion. This mechanism thus mimics a choline-deficient diet. This microbiota-related reduced choline bioavailability may result in the inability to synthesize PC necessary for the assembly and secretion of very-low-density lipoprotein (VLDL) and subsequent accumulation of TG in liver. Methylamines also induce hepatotoxicity and hepatocarcinogenicity in rats.

Because bacterial avidity for B12 is similar to that of human IF, the extent that bacteria competes with IF in the gut for B12 suggests that IF may have a physiologic function in addition to that of promoting absorption of B12 across the ileal mucosa, namely that of protecting B12 from uptake and utilization by the normal flora of the terminal small bowel. This is only the case however for ingested quantities of Cbl that can find native IF capacity for binding. Once the amount of Cbl ingested is a mega dose (500-5,000 ug per dose or per day), there will never be enough IF capacity secreted for binding protection against bacterial uptake and analogue synthesis. A survey of over 300 sequenced microbiota-derived bacterial genomes shows that at least 83% of sequenced strains surveyed possess enzymes that are dependent on vitamin B12. De novo biosynthesis of corrinoids takes a staggering number of enzymatic steps (≈30), so it is not surprising that only a small set of gut microbes produce these molecules, while the remainder scavenge them from other microbes or the host's diet. Therefore, a massive excess of unabsorbed vitamin B12 can substantially contribute to an overgrowth phenomenon amongst more competitive B12 microbes and thereby influence choline availability for absorption. As a result, a preferred composition with choline will be with a physiologic (and not pharmacologic massive dose) of vitamin B12 with Intrinsic Factor.

Neural tube defects are birth defects of the brain, spine, or spinal cord. Neural tube defects happen in the first month of pregnancy. The two most common neural tube defects are spina bifida and anencephaly. In spina bifida, the fetal spinal column does not close completely. There is usually nerve damage that causes at least some paralysis of the legs. In anencephaly, most of the brain and skull do not develop. Babies with anencephaly are usually either stillborn or die shortly after birth. Another type of defect, Chiari malformation, causes the brain tissue to extend into the spinal canal. A subject may be at risk for having a fetus with neural tube defects. Non-limiting examples of risk factors for neural tube defects in the fetus include obesity, diabetes, and/or antiseizure medicines. A subject may be diagnosed as having a fetus with neural tube defects. Non-limiting examples of methods to diagnose a fetus with neural tube defects include lab tests ("triple screen" blood test, amniotic fluid test) or imaging tests (ultrasound, X-ray, MRI, CT scan). If a subject has been diagnosed as having a fetus with neural tube defects, a composition of the disclosure may be used to prevent further damage.

Another aspect of the disclosure provides a method for providing adequate choline during neural and brain development of the last trimester and up to 6 months of postnatal life of the infant, preferably up to 12 months, more preferably up to 24 months of postnatal life. High choline intake can be insured by increasing the choline intake of the mother who then transfers a high choline intake to the child by via breast milk. It has been demonstrated that this perinatal period is critical for cholinergic organization of the brain and insuring a high choline intake during this period will increase memory capacity and precision of young adults as well as prevent cognitive, attention and memory decline during advanced age. In other words, the metabolic imprinting that takes place with choline administered in adequate amounts during the last few months or pregnancy and first few years of life will have an enduring effect on the cognitive and memory performance and preservation during young and old adult life respectively.

Another aspect of the disclosure provides a method for reducing the risk of non-alcoholic fatty liver disease in a human subject receiving supplemental iron in a total elemental iron amount of about 20 mg to about 150 mg per day. The method comprises orally administering an amount of choline in a form of one more physiologically acceptable salt in a total amount of about 55 mg to about 5000 mg. The composition may further comprise intrinsic factor in an amount of about 35 µg to about 10,000 µg. Various aspects of the composition are described in Section I. Non-alcoholic fatty liver disease is described above. The non-alcoholic fatty liver disease may be due to too much iron or "iron overload". Iron overload is an excess (too much) iron in the body. Excess iron in vital organs, even in mild cases of iron overload, increases the risk for liver disease (NAFLD, cirrhosis, hepatocellular carcinogenesis), colonic neoplasia, colorectal carcinogenesis, atherosclerosis, heart attack or heart failure, insulin resistance, diabetes mellitus, osteoarthritis, osteoporosis, metabolic syndrome, hypothyroidism, hypogonadism, and hypopituitarism, numerous symptoms and in some cases premature death. Iron mismanagement resulting in overload can accelerate such neurodegenerative diseases as Alzheimer's, early-onset Parkinson's, Huntington's, epilepsy and multiple sclerosis. Iron overload can be inherited (genetic) or acquired by receiving numerous blood transfusions, getting iron shots or injections, or consuming high levels of supplemental iron.

Accordingly, another aspect of the disclosure provides a method for mitigating the risk for metabolic, cardiovascular and hepatic diseases in a human subject with Dysmetabolic Iron Overload Syndrome (DIOS). The method comprises orally administering an amount of choline in a form of one more physiologically acceptable salt in a total amount of about 5 mg to about 5000 mg. The composition may further comprise intrinsic factor in an amount of about 35 µg to about 10,000 µg. Various aspects of the composition are described in Section I. DIOS is characterized by an elevated serum ferritin with a normal transferrin-iron saturation percentage. A subject with DIOS will likely also have an elevated GGT (liver enzyme) possibly due to a fatty liver. Non-limiting examples of metabolic, cardiovascular and hepatic disease due to DIOS include liver disease (NAFLD, cirrhosis, hepatocellular carcinogenesis), colonic neoplasia, colorectal carcinogenesis, atherosclerosis, heart attack or heart failure, insulin resistance, diabetes mellitus, osteoarthritis, osteoporosis, metabolic syndrome, hypothyroidism, hypogonadism, and hypopituitarism. By mitigating the risk for metabolic, cardiovascular and hepatic disease in a human subject with DIOS, a composition of the disclosure may reduce, alleviate or prevent the signs and symptoms associated with iron overload. Non-limiting examples of signs and symptoms of iron overload include chronic fatigue, joint pain, abdominal pain, irregular heart rhythm, skin color changes (bronze, ashen-gray green), loss of period, loss of interest in sex, hair loss, enlarged liver or spleen, impotence, infertility, depression, adrenal function problems, early onset neurodegenerative disease, elevated blood sugar, elevated liver enzymes, and elevated iron (serum iron, serum ferritin).

In an aspect, the disclosure provides a method for reducing intracellular iron accumulation and/or reducing the negative effects associated with intracellular iron accumulation. The method comprises administering to the subject a single dosage form composition comprising (a) intrinsic factor in an amount of about 35 µg to about 10,000 µg; and (b) choline in a form of one or more physiologically acceptable salts, phospholipid bound forms, intermediates or derivatives thereof, and in a total amount of choline that is at least 55 mg to about 5000 mg, wherein the subject has a diagnosis of iron overload. Various aspects of the composition are described in Section I.

Another aspect of the disclosure provides a method for supplementing iron to a human subject. The method comprises administering to the subject a single dosage form composition comprising (a) iron in a form of one or more physiologically acceptable iron compounds, chelates, complexes, or admixtures, and in a total elemental iron amount of about 10 mg to about 500 mg; and (b) choline in a form of one or more physiologically acceptable salts, phospholipid bound forms, intermediates or derivatives thereof, and in a total amount of choline that is at least 50 mg to about 5000 mg, wherein the subject has (i) iron deficiency and (ii) either an increased risk for, or is diagnosed with, non-alcoholic fatty liver disease, metabolic syndrome, or type 2 diabetes mellitus. Various aspects of the composition are described in Section I.

In other embodiments, a subject with iron deficiency may also have either an increased risk for, or is diagnosed with hepatocellular carcinogenesis, colonic neoplasia, colorectal carcinogenesis, atherosclerosis, or dysmetabolic iron overload syndrome.

As used herein, a subject with an iron deficiency is a subject obtaining insufficient amounts of iron. The Recommended Dietary Allowance (RDA) is the average daily level of intake sufficient to meet the nutrient requirements of nearly all (97%-98%) healthy individuals. The RDA for iron for male and female human subjects age birth to 6 months is 0.27 mg, age 7 to 12 months is 11 mg, age 1 to 3 years is 7 mg, age 4 to 8 years is 10 mg, and age 9 to 13 years is 8 mg. The RDA for iron for a male human subject age 14 to 18 years is 11 mg and age 19-51+ years is 8 mg. The RDA for iron for a female human subject age 14 to 18 years is 15 mg, age 19-50 years is 18 mg, and age 51+ is 8 mg. The RDA for a female human subject during pregnancy is 27 mg and during lactation is 9 to 10 mg. These values are 1.8 times higher for vegetarians. Accordingly, a subject with an iron deficiency is any subject obtaining below these amounts.

A subject with an iron deficiency may be a subject at risk of having iron deficiency or a subject diagnosed with iron deficiency. Non-limiting examples of subjects at risk of having iron deficiency include infants, young children, teenaged girls, pregnant women, premenopausal women, women with heavy menstrual bleeding, frequent blood donors, cancer subjects, heart failure subjects, and subjects with poor diets, malabsorptive disorders and/or blood loss. Additionally, race and sociodemographic factors may increase a subject's risk of having iron deficiency. For example, iron deficiency is more common among children and adolescents in food-insecure households than in food-secure households. Further, among pregnant women, iron deficiency is more common in Mexican American and non-Hispanic black women than in non-Hispanic white women.

A subject with an iron deficiency may have mild deficiency, marginal deficiency or iron-deficiency anemia (IDA). In a subject with mild deficiency or storage iron depletion, serum ferritin concentrations and levels of iron in bone marrow decrease. In a subject with marginal deficiency, mild functional deficiency, or iron-deficient erythropoiesis (erythrocyte production), iron stores are depleted and iron supply to erythropoietic cells and transferrin saturation decline, but hemoglobin levels are usually within the normal range. In addition, plasma iron levels decline and plasma transferrin concentrations (measured by plasma total iron-binding capacity) rise, resulting in decreased transferrin saturation. Serum transferrin receptor concentrations also increase. In a subject with IDA, iron stores are exhausted; hematocrit and levels of hemoglobin decline; and the resulting microcytic, hypochromic anemia is characterized by small red blood cells with low hemoglobin concentrations. IDA is defined as a hemoglobin level that is lower than two standard deviations from the mean distribution in a healthy population of the same gender and age living at the same altitude. Functional deficits associated with anemia include gastrointestinal disturbances and impaired cognitive function, immune function, exercise or work performance, and body temperature regulation. In infants and children, IDA can result in psychomotor and cognitive abnormalities that, without treatment, can lead to learning difficulties.

A subject with an iron deficiency also has either an increased risk for, or is diagnosed with, non-alcoholic fatty liver disease, metabolic syndrome, or type 2 diabetes mellitus. NAFLD and metabolic syndrome are described above. Type 2 diabetes mellitus, also sometimes referred to as adult-onset or noninsulin-dependent diabetes, is a chronic condition that affects the way the body metabolizes sugar (glucose). With type 2 diabetes, the body either resists the effects of insulin or does not produce enough insulin to maintain a normal glucose level. A subject may be at risk for type 2 diabetes mellitus. Non-limiting examples of risk factors for type 2 diabetes mellitus include overweight, fat distribution (abdomen), inactivity, family history of type 2 diabetes, race (black, Hispanic, American Indian, Asian-American), age (greater than 45), prediabetes (gestational diabetes), and polycystic ovarian syndrome. A subject may be diagnosed with type 2 diabetes mellitus. Non-limiting examples of symptoms useful in the diagnosis of type 2 diabetes mellitus include increased thirst and frequent urination, increased hunger, weight loss, fatigue, blurred vision, slow-healing sores or frequent infections, and/or areas of darkened skin. Additional methods for diagnosing type 2 diabetes mellitus include glycated hemoglobin (A1C) test, random blood sugar test (200 mg/dL or higher), fasting blood sugar test (100 to 125 mg/dL is considered prediabetes and 126 mg/dL or higher is considered diabetes), oral glucose tolerance test (140 to 199 mg/dL indicates prediabetes and 200 mg/dL or higher indicates diabetes).

(a) Administration

A composition of the disclosure may be administered once a day or more than once per day such as for example but not limited to morning administration and evening administration. Humans or other animals may be treated with compositions of the present invention using continuous administration or varying administration over the course of treatment. "Continuous administration" is the administration of a single composition formulation throughout the course of treatment. "Varying administration" is the administration of different composition formulations on different days, and/or administration of different composition formulations within a 24-hour period.

Suitable administration schedules or dosing regimens for methods described herein also include administering one or more compositions of the present disclosure for about twenty-one days and then discontinuing iron supplementation for about seven days prior to again initiating iron supplementation. Such a dosing regimen is referred to herein as "cyclical administrations". Alternatively, one or more compositions of the present disclosure may be administered for about twenty days with discontinued iron supplementation for about 10 days, administered for about a week with discontinued iron supplementation for about a week, and the like. It is important to note that the present disclosure is not intended to be limited to administering one or more of the subject compositions for a specific number of days and then discontinuing iron supplementation for a specific number of days. Rather, iron supplementation is administered and discontinued for an amount of time necessary to affect a decrease in a labile pool of iron in small intestine mucosal cells. By affecting a decrease in the labile pool of iron in the small intestine mucosal cells, the potential for iron absorption by the small intestine mucosal cells is increased. During periods of discontinued iron supplementation, nothing, placebo, a non-iron containing composition comprising iron absorption promoters, vitamins, and/or minerals, one or more compositions useful in the treatment of one or more diseases associated with iron deficiency, or a combination thereof, may be administered.

The compositions disclosed herein may be used independently or used in combination with standard treatments for any of the diseases or disorders disclosed herein. For example, in addition to the single dosage form composition, subjects may be treated with standard treatments for NAFLD, metabolic syndrome and type 2 diabetes mellitus. Non-limiting examples of standard treatments for NAFLD include healthy diet, exercise, lower cholesterol, lower triglycerides, control diabetes, and/or avoid alcohol. Non-limiting examples of standard treatments for metabolic syndrome include healthy eating, healthy weight, managing stress, physical activity, quitting smoking, medicines to control high blood pressure, high triglycerides, low HDL cholesterol and high blood sugar. Non-limiting examples of standard treatments for type 2 diabetes mellitus include healthy eating, regular exercise, diabetes medication and insulin therapy (metformin, sulfonylureas, meglitinides, thiazolidinediones, DPP-4 inhibitors, GLP-1 receptor agonists, SGLT2 inhibitors) blood sugar monitoring, and/or bariatric surgery.

EXAMPLES

The following examples illustrate various iterations of the invention. However, those of skill in the art should, in light of the present disclosure, appreciate that many changes can be made in the specific embodiments which are disclosed and still obtain a like or similar result without departing from the spirit and scope of the invention.

Example 1. Composition 1

Exemplary composition for a prenatal human subject or human subject trying to conceive:

| | |
|---|---|
| 40 mg Sumalate | (200 mg) |
| 125 mg VitaCholine | (312 mg) |
| 1 mg folate | (1.3 mg) |
| 3.6 µg $B_{12}$ | (0.3 mg) |
| 135 µg Intrinsic Factor | (72 mg) |

Optionally: Tablet

| | |
|---|---|
| Cellulose | (300 mg) |
| Crosscarmelose | (40 mg) |
| Stearic Acid | (30 mg) |
| Silicon Dioxide | (10 mg) |
| Magnesium Stearate | (8 mg) |
| Total Weight | (972 mg) |

Example 2. Composition 2

Exemplary composition for a lactating human subject:

| | |
|---|---|
| 20 mg Sumalate | (100 mg) |
| 200 mg VitaCholine | (285 mg) |
| 1 mg Folate | (1.3 mg) |
| 3.6 µg $B_{12}$ | (0.3 mg) |
| 135 µg IF | (72 mg) |

Optionally: Tablet

| Silicon Dioxide | (1 mg) |
|---|---|
| Magnesium Stearate | (8 mg) |
| Total Weight | (467 mg) |

Example 3. Composition 3

Exemplary composition for a subject with metabolic syndrome:

| 20 mg Sumalate | (100 mg) |
|---|---|
| 200 mg VitaCholine | (285 mg) |
| 180 μg Menaquinone (Vit K$_2$) | (5 mg) |
| 50 mg Magnesium glycinate-buffered | (277 mg) |
| 0.8 mg Folate | (1 mg) |
| 9 μg B$_{12}$-350 μg IF | (172.5 mg) |

Optionally:

| Silicon Dioxide | (10 mg) |
|---|---|
| Magnesium Stearate | (8 mg) |
| Total Weight | (858 mg) |

What is claimed is:

1. A single dosage form composition, the single dosage form composition comprising: (a) recombinant human intrinsic factor in an amount of about 35 μg to about 950 μg; and (b) choline in a form of one or more physiologically acceptable salts, phospholipid bound forms, intermediates or derivatives thereof, and in a total amount of choline molecule that is at least 75 mg to about 5000 mg.

2. The single dosage form composition of claim 1, wherein the recombinant human intrinsic factor is a rhIF-B$_{12}$ complex.

3. The single dosage form composition of claim 1, wherein the total amount of choline molecule is at least 75 mg to about 1500 mg.

4. The single dosage form composition of claim 1, wherein the choline is a choline salt, and the choline salt has a choline cation concentration that is greater than 40% by weight, greater than 50% by weight, greater than 60% by weight, greater than 70% by weight, greater than 75% by weight, or greater than 80% by weight.

5. The single dosage form composition of claim 1, wherein the choline is choline bitartrate.

6. The single dosage form composition of claim 5, wherein the choline bitartrate comprises the L-isomer of bitartrate.

7. The single dosage form composition of claim 5, wherein the choline bitartrate comprises the racemic mixture of the D- and L-isomers of bitartrate.

8. The single dosage form composition of claim 5, wherein the choline bitartrate comprises the natural form of bitartrate.

9. The single dosage form composition of claim 6, wherein the composition is optically active to polarizing light.

10. The single dosage form composition of claim 9, wherein polarizing light is rotated more than +17.5 degrees.

11. The single dosage form composition of claim 7, wherein the composition is optically inactive to polarizing light.

12. The single dosage form composition of claim 11, wherein polarizing light is rotated less than +17.5 degrees.

13. The single dosage form composition of claim 1, wherein the choline is choline chloride.

14. The single dosage form composition of claim 1, wherein the choline is choline dihydrogen citrate.

15. The single dosage form composition of claim 1, further comprising iron in a form of one or more physiologically acceptable iron compounds, chelates, complexes, or admixtures, and in a total elemental iron amount of about 5 mg to about 150 mg.

16. The single dosage form composition of claim 15, wherein the total amount of elemental iron is about 10 mg to about 150 mg, about 20 mg to about 150 mg, about 30 mg to about 150 mg, or about 40 mg to about 150 mg.

17. The single dosage form composition of claim 15, wherein the total amount of elemental iron is about 50 mg to about 150 mg.

18. The single dosage form composition of claim 15, wherein the iron is an iron amino acid chelate.

19. The single dosage form composition of claim 18, wherein the iron amino acid chelate is ferrous asparto glycinate or ferrous bisglycinate.

20. The single dosage form composition of claim 1, wherein the composition further comprises one or more additional minerals, vitamins, fatty acids, amino acids, or combinations thereof.

* * * * *